(12) United States Patent
Pearson et al.

(10) Patent No.: US 7,476,379 B1
(45) Date of Patent: *Jan. 13, 2009

(54) EMU-BASED FORMULATIONS FOR THE TREATMENT OF DAMAGED SKIN BY INHIBITING MICROBIAL AND FUNGAL ACTIVITY

(75) Inventors: Maurine Pearson, Pilot Point, TX (US); Teresa Leigh Barr, Hood River, OR (US)

(73) Assignee: Pearson Research & Development Limited, Pilot Point, TX (US)

( * ) Notice: Subject to any disclaimer, the term of this patent is extended or adjusted under 35 U.S.C. 154(b) by 170 days.

This patent is subject to a terminal disclaimer.

(21) Appl. No.: 11/353,535

(22) Filed: Feb. 13, 2006

Related U.S. Application Data

(63) Continuation-in-part of application No. 10/752,820, filed on Jan. 7, 2004, now Pat. No. 6,998,109.

(51) Int. Cl.
*A01N 25/02* (2006.01)
*A01N 57/00* (2006.01)
*A61K 9/00* (2006.01)
*A61K 31/66* (2006.01)
*A61K 35/12* (2006.01)

(52) U.S. Cl. ............ 424/43; 424/400; 424/520; 424/522; 514/104

(58) Field of Classification Search ............ 424/43, 424/400, 520, 522; 514/104
See application file for complete search history.

(56) References Cited

U.S. PATENT DOCUMENTS 4,557,934 A * 12/1985 Cooper ............ 514/159
6,528,040 B1 * 3/2003 Pearson et al. ............ 424/43
6,998,109 B1 * 2/2006 Pearson et al. ............ 424/43

* cited by examiner

*Primary Examiner*—Alton N Pryor
(74) *Attorney, Agent, or Firm*—Buskop Law Group, PC; Wendy Buskop

(57) ABSTRACT

A formula for use in treating skin aliments includes from about 20 to about 75 wt % emu oil; from about 0.10 to 33 wt % benzyl alcohol; from about 0.10 to about 33 wt % benzoin derivative; from about 0.2 to about 2 wt % allantoin; from about 0.25 to about 1.25 wt % methylparaben; from about 1.0 to about 13 wt % alkyl esters; and from about 0.01 to about 0.30 wt % propylparaben. The formula can be applied to skin of animals or humans with skin ailments. The formula can be applied is various manners, such as through an enhanced oil, a spray, an elastomeric device, a wipe, a lotion, an ointment, a cream, a gel or combinations thereof.

4 Claims, No Drawings

EMU-BASED FORMULATIONS FOR THE TREATMENT OF DAMAGED SKIN BY INHIBITING MICROBIAL AND FUNGAL ACTIVITY

CROSS REFERENCE TO RELATED APPLICATIONS

The present application is a continuation-in-part and claims priority from patent application Ser. No. 10/752,820, filed on Jan. 7, 2004 now U.S. Pat. No. 6,998,109.

FIELD

The embodiments relate to Emu oil based formulas that are analgesic, anesthetic and anti-pruritic formulations and also treat microbial and fungal infections of humans and animals such as skin irritations, wounds and burns.

BACKGROUND

Found in the wild only in Australia, Emus (*dromiceius novae-hollandiae*) are the second largest members of the ratite group of flightless birds in the world. The Emu have wings but they are very tiny. They can run up to 35-40 miles an hour, as they have very large and strong legs. Although a very docile creature, the Emu's legs are so strong; one kick can break a man's leg. Now Emus are being farmed in many parts of the world. They are raised for their valuable products, which include very low fat meat, supple leather hides, decorative and nutritional eggs, and very rich oil, which are obtained from the Emu. Emus are by nature, very healthy and immune to many diseases. Emus are referred to as "living dinosaurs," as their skeletal structure closely resembles some dinosaurs. Emus living today closely resemble their ancestors of millions of years ago.

Emu oil, a food by product, is obtained from the fat of the Emu. It is an all-natural substance. When processed, the fat is taken through a series of steps to refine, sterilize and deodorize the oil. Not all Emu oil on the market is refined. Some Emu oil is simply rendered, which means the oil is simply filtered, and can contain contaminants. Emu oil contains high amounts of EFA's (essential fatty acids). EFA's produce energy in the process of oxidation. In humans EFA's govern growth, vitality and mental state of mind. Oxidation is the central and most important living process in our body.

Emu oil by nature is not regarded as a sterile ingredient. Due to lack of regulatory controls and procedures, Emu oil is processed in many different ways, i.e., some forms of rendering, which is simply a filtration process, which leaves the Emu oil with its natural yellow color, and a slight odor. The present formulation uses a refinement process, which yields a clearly pure Emu oil product, creamy white and odor free. The present formulation utilizes a sterilization technique to render the Emu oil in the present formulation free of contaminants to be used as a preparation and treatment for chronic cutaneous wounds, venous stasis ulcers, pressure wounds and burn ulcers.

Various patents discuss the use of Emu oil, for example, U.S. Pat. No. 5,662,921 discusses how Emu oil can be use to prevent scarring when applied to a newly received cut or burn. It has been known for a long time that Emu oil also diminishes old scars, even stretch marks. U.S. Pat. No. 5,662,921 discusses how Emu oil increases high-density lipoproteins, preventing and treating scarring. U.S. Pat. No. 5,958,384 teaches that topical or parenteral administration of Emu oil to a mammal stimulates the proliferation of skin, as well as rejuvenating photo-damaged skin. This same patent teaches that Emu oil also stimulates melannogenesis in the skin and it can be used to treat disorders such as hypo-pigmentation.

A need exists for a formula, using Emu oil which can be used in hospitals, as a sterile formula for treating of various wounds, burns, and other dermatological problems, while remaining stable and usable over time without degradation.

A need exists for a formulation that also relieves the pain on the epidermis of skin irritations, various wounds and burns.

U.S. Pat. No. 6,071,959 teaches that amide-type local anesthetics have been used medically for many years and is hereby incorporated as reference. They produce a reversible loss of sensation by preventing or diminishing the conduction of sensory nerve impulses near to the site of their administration. They are most often used to ameliorate pain without loss of nervous control. Examples of amide-type local anesthetics are aptocaine, benzocaine, bupivacaine, butanilicaine, carticaine, cinchocaine, clibucaine, ethyl parapiperidinoacetylaminobenzoate, etidocaine, lignocaine (also known as lidocaine), mepivacaine, oxethazaine, prilocalne, pyrrocaine, ropivacaine, tolycaine and vadocaine.

Amide-type local anesthetics can be administered in a wide variety of different ways; some compounds are more suitable than others for a particular route of administration. For example, topical anesthesia works by blocking the sensory nerve endings in the skin or mucous membranes. The amide-type local anesthetics also vary in their anesthetic potency, rate of onset and duration of effect. For example, lignocaine (2-diethylamino-N-[2,6-dimethylphenyl]acetamide) has a fast onset and an intermediate duration of action, and is employed in a wide range of anesthetic applications.

DETAILED DESCRIPTION OF THE EMBODIMENTS

Before explaining the present embodiments in detail, it is to be understood that the embodiments are not limited to the particular embodiments and that they can be practiced or carried out in various ways.

The embodied formulations are Emu oil based formulas that are analgesic, anesthetic and anti-pruritic formulations and also treat microbial and fungal infections of humans and animals such as skin irritations, wounds and burns. The formulations can be applied to the skin of animals with skin ailments. Examples of animals that the formulations can be safely applied to include canines, felines, equines, bovines, swine, bovid ruminants, ovine, avian species, and the like.

The formulations can be applied in numerous manners. Examples of applications types include through an enhanced oil, a spray, an elastomeric device, a wipe, a lotion, an ointment, a cream, a gel or combinations thereof. In some embodiments, the formulations can be topical anti-microbial formulas or topical anti-fungal formula. The embodied formulations aid in healing skin ailments including, but not limited to ringworm, fungus, hot spots, and dry skin. The embodied formulations aid in healing wounds including, but not limited to injuries, bites, grafts, incest stings, allergies, and hoof injuries.

When applied to the skin, the formulations—as examples—can provide complete wound closure for chronic, non-healing wounds, can accelerate wound healing by diminishing time required to obtain complete wound closure by applying the formula to the skin, and can heal burns and donor site wounds. The embodied formulations can heal skin ulcers, venous stasis, bedsores, diabetic ulcers, and combinations thereof.

The embodied formulations are adapted to inhibit *Trichophyton Rubrum, Microsporum Equinum, Trichophyton Equinum, Microsporum Gypseum, Microsporum Canis, Epidermophyton Floccosum, Trichophyton Mentagrophytes* or combinations thereof.

The clinical benefits of this formula include reduced wound sepsis rates, improved hempdynamic status, and decreased requirement for donor site harvest. Since engraftment rates are high with good standard care, it is important to evaluate healing outcomes such as durability, functionality, and cosmetic appearance, including scarring. The formula also provides improved quality of healing and products that reduce scarring can also improve function, for example, range of motion, the contour and feel of healed skin, or normalization of skin pigmentation or markings.

The clinical benefits of the embodied formulations include increased healing times due to the anti-microbial and antifungal activity of the present formulation.

The clinical benefits of the embodied formulations include providing a naturally protective barrier that keeps the skin moist and supple while healing, thereby reducing scratching, infection and scarring.

The clinical benefits of the embodied formulations include the prevention and treatment of microbial and fungal infections, on the surface of the skin and keratin, as well as deep into wounds, lesions and ulcers, as well as necrotic tissue. Keratin is a fibrous insoluble protein that is the main structural element in hair, feathers, nails and hooves. The embodied formulations have been clinically proven to penetrate keratin, such as hair feathers, nails and hooves. Source: Microbiology Laboratory, University of North Texas.

The embodied formulations enable tissue to regenerate, restore, and rebuild in the underlying wound itself and surrounding tissue, therefore fortifying, increasing energy to the existing cells that are not necrotic, and fortifying cells that are necrotic. The formulation is able to improve wound closure time, and facilitation of surgical closures, as well as to treat and prevent microbial and fungal infections on body and keratin surfaces as well as within various wounds and burns.

In one embodiment, the formula is an Emu oil based formula that is capable of improved transdermal properties, thus creating healthier cells that proliferate at an accelerated rate. By increasing the feeding of the skin cells, this causes proliferation and thus the theory of Emu oil being biologically active to human skin. The embodied formulations can include lidocaine to relieve the pain on the epidermis of humans and animals of skin irritations, wounds and burns.

The formulations can include from about 20 to about 75 wt % emu oil; from about 0.10 to about 33 wt % benzyl alcohol; from about 0.10 to about 33 wt % benzoin derivative; from about 0.2 to about 2 wt % allantoin; from about 0.25 to about 1.25 wt % methylparaben; from about 1.0 to about 13 wt % alkyl esters; and from about 0.01 to about 0.30 wt % propylparaben. The formulations can further include from about 0.01 to about 20.0 wt % of caine anesthetics. Caine anesthetics can include aptocaine, benzocaine, bupivacaine, butanilicaine, carticaine, cinchocaine, clibucaine, ethyl parapiperidinoacetylaminobenzoate, etidocaine, lignocaine (also known as lidocaine), mepivacaine, oxethazaine, prilocalne, pyrrocaine, ropivacaine, tolycaine, or vadocaine.

In alternative embodiments, the formulation can include from about 10.0 wt % to about 75.0 wt % Emu oil; from about 0.10 wt % to about 33.0 wt % benzoin and derivatives thereof; from about 0.01 wt % to about 40.0% analgesics; from about 0.01 to about 13 wt % alkyl esters; from about 0.10 wt % to about 5.0 wt % allantoin; from about 0.1 wt % to about 5.0 wt % methylparaben; and from about 0.1 wt % to about 2.0 wt % propylparaben. The embodied formulations can include sufficient and effective amounts of environmentally safe propellants.

The embodied formulations can be an analgesic, anesthetic and anti-pruritic formulations. The formulations can include from about 0.10 wt % to about 20.0 wt % of lidocaine or analgesic. The lidocaine relieves pain on the epidermis of humans and animals of skin irritations, various wounds, or burns. The formulation is adapted to inhibit microbial activity from *Escherichia coli, Salmonella typhimurium, Pseudomonas aeruginosa, Staphylococcus Aureus, Enterococcus Faecalis, Bacillus Cereus, Candida Albicans, Streptococcus Agalactiae* or combinations thereof. Source: Microbiology Laboratory, University of North Texas.

An example formulation can include about 61.5 wt % Emu Oil; about 20.0 wt % Benzyl Alcohol; about 13.0 wt % Benzoin Derivative with a branched Alkyl Ester; about 2.0 wt % Allantoin; about 1.25 wt % Methylparaben; about 0.40 wt % Propylparaben; and about 2.0 wt % Lidocaine or analgesic.

One example of emu oil that can be used in the embodied formulations can have a chemical analysis of about 0.33% to 0.02% Free Fatty Acid; about 0.66% Acid Value; a calculated Iodine value between 69.7 and 72.8 mEq/100 g; and an OSI of 11.95 Hours at 110.0 degrees C.

Table 1 illustrates the fatty acid composition of the Emu oil as compared to human skin.

TABLE 1

Fatty Acid Composition -- Emu Oil VS Human Skin Oil

| | | Emu Oil | Human Skin Oil |
|---|---|---|---|
| Myristic | C:14:0 | 0.3% | 2.1% |
| Palmitic | C:16:0 | 20.3% | 20.2% |
| Palmitoleic | C:16:1 | 3.2% | 3.8% |
| Margaric | C:17:0 | 0.2% | |
| Margaric oleic | C:17:1 | 0.1% | |
| Stearic | C:18:0 | 10.1% | 11.2% |
| Oleic | C:18:1 | 51.6% | 30.8% |
| Linoleic | C:18:2 | 13.1% | 15.1% |
| Linolenic | C:18:3 | 0.5% | 0.3% |
| Arachidic | C:20:0 | 0.1% | |
| Eicosinoac | C:20:1 | 0.5% | |

Analysis of the Emu oil shows calculated iodine content of 72.8%. The present formulation embodies the natural iodine properties of the Emu oil. Iodine has long been known for antiseptic and germicide properties, in turn helping to accelerate wound closure by minimizing infection. Normally, iodine does not occur naturally in nature. In combination as iodides, iodine is found in the ashes of certain marine algae and weeds. Until recently, the most important source of iodine was crude Chile saltpeter, and now has been found in the brine of oil wells. Elementary iodine is toxic. The iodine content in the Emu oil is a naturally occurring property, and no reports of toxicity have been noted. Examples of other fatty acids, which can be found in Emu oil, include elaidic and vaccenic fatty acids.

The embodied formulations use of the iodine in the Emu oil as an enhancement to the germicide, fungicide and all around antiseptic properties of the formulation. Topical skin dosages of iodine can be used full strength or diluted to 0.1% for applications to wounds. The therapeutic index for iodine is among the highest of the antiseptics. Unfortunately, iodine burns are common and largely the result of the use of tinctures and solutions with concentrations higher than tolerated by certain skin types. The embodied formulations embody the features, values and benefits of the high iodine content of the Emu oil, in its natural state, and in combination with the Emu oil fatty acid composition, creating a buffer against the harmful side effects of typical iodine.

An analysis of fatty acids in Emu oil reveals that the oil contains approximately 70% unsaturated fatty acids. The major fatty acid found in Emu oil is oleic acid, which is monosaturated and which comprises over 40% of the total fatty acid contents. This fatty acid is a known enhancer for penetration and transportation of compounds through the pores of the epidermis, the membrane of the skin, and, thus, delivering the active ingredients into the lipid layer at the cellular level.

Emu oil also contains both of the two EFA's, which are important to human health and include: 20% linoleic and 1-2% linolenic acid. Essential fatty acids are by definition those fatty acids that must be obtained from our diet since the body cannot manufacture them, hence, making them essential as transdermal supplements to nourish and proliferate new skin cells for chronic cutaneous ulcers and burn wounds. As one can see in the analysis of Emu oil to human skin oil in Table 1, Emu oil closely resembles human skin oil and is a natural food for skin cells.

Emu oil is unique, as most land animals have a higher concentration of saturated fats. Typical fat contains both saturated and unsaturated fatty acids. The fats found in land animals have a higher percentage of side chains than do the fats in sea animals. Although unsaturated fats are less efficient storage sites for food energy because they have fewer CH bonds than do saturated fats, they have a distinct advantage for animals that live in cold water. Saturated fats melt at higher temperatures than do unsaturated fats. In cold waters, sea animals with solid fats would have the reduced ability to move. This theory is subject to analysis, and can prove it is easier to transport unsaturated fats through the skin structure and membrane into the lipid layer, rather than a saturated fat.

The monosaturated fatty acid, oleic acid, is the major fatty acid in Emu oil. This fatty acid is a known enhancer for penetration and transportation of compounds through the pores, the membrane of the skin, and, thus, delivering the active ingredients into the lipid layer at the cellular level. This process is also known as transdermal facilitation.

Essential fatty acids (EFA's) play two important roles in human physiology. Both derive from their incorporation into the phospholipids of cell membranes. By virtue of their high degree of unsaturation, and, hence low melting points, they decrease membrane viscosity and affect several aspects of membrane function. Nearly all cells contain basic fat and oil substances. Fats are called energy storehouses, as on a weight-by-weight basis; they contain twice as much energy as a carbohydrate or protein. Fats are also a heterogeneous group of compounds, which are characterized by their solubility in solvents such as ether and therefore insoluble in water. Emu oil is rendered primarily from the fat pads of the bird or from what is referred to as the storage lipids. Emu fat is storage fat, as in most animals and organisms, which means it is the principal form of stored energy. As an energy source, it is completely combustible to carbon dioxide and water. This releases a quantity of energy similar to the combustion of fossil fuel.

The fats, which are not reactive to sodium or potassium, are referred to as unsaponificable fats. The major portion of unsaponificable fraction is the sterols. These are cholesterol and cholesterol like substances, which have a characteristic chemical composition, which can simply be described as closed ring in contrast to the chain or open ring appearance of the triglycerides and fatty acids. The cholesterol molecule is the classic steroid molecule. This molecule is common to a number of chemicals important to humans, for example, the anti inflammatory steroidal hormones such as hydrocortisone, and androgens such as testosterone, the progestogens, the bile acids, the vitamin D, and estrogen. The restoration of hormonal balance has been attributed to the restoration of many normal functions of the body, as well as general health care and maintenance.

Inflammation is the normal response to healing chronic ulcers and burn wounds. Inflammation also causes drying, scabbing and scar tissue to form. A product that could decrease wound sensitivity and inflammation, but increase moisture content would be desirable. Adequate lubrication aids the healing process by providing moisture in areas where sebaceous glands are depleted or currently dysfunctional, increasing pliability of the wound area, thus improving pigmentation and vascularity, which also aids in reducing scar tissue as well restoring the pigmentation of hair, skin and keratin.

Inflammation is produced in the body as a reaction to injury or infection. The embodied formulations, when topically applied to the skin, increase the synthesis of DNA in the epidermis, which is a measure of increase in the proliferation activity of the dermis. The presence of Oleic acid, a simple triglyceride that contains only one type of fatty acid (oleic acid) enables the present formulation to work effectively. A triglyceride is comprised of a glycerin backbone to which the fatty acids are attached. Naturally occurring triglycerides usually are mixed triglycerides (for example, contain more than one fatty acid). An example of a mixed triglyceride is palmmitodiolein, the fatty acid composition of which is, as the name indicates, one molecule of palmitic acid and two molecules of oleic acid. This triglyceride can have structural arrangements other than the one shown, i.e., the fatty acid molecules can be arranged with palmitic acid occupying any of the two possible different positions. An example oleic acid is a monosaturated fat.

In an embodiment of the formulation, the Emu oil is a refined and sterilized Emu oil. The refined and sterilized Emu oil can range from about 60 wt % to about 65 wt % in the formulation. The refined and sterilized Emu oil can include at least 70 wt % linoleic and linolenic acids in combination. The refined and sterilized Emu oil in the formulation can also include 20 wt % linoleic and 1-2 wt % linolenic acid.

Linoleic acid is an essential polyunsaturated fatty acid. Linoleic acid deficiency symptoms include scaly skin and slow to heal wounds. Linoleic acid supplementation can be essential and crucial to fortify slow to heal wounds and strengthen and rebuild the skin by increasing linoleic acid content through the membrane and into the lipid layer, thus allowing and enhancing new skin cell and membrane proliferation, as well as minimizing scar tissue. Linoleic acid is required for the formation and maintenance of the epidermal barrier. The present formulation requires linoleic acid.

The embodied formulations can include linoleic acid, which when transferred to the lipid layer can be crucial to "feeding" the skin cells, thereby creating more energy to burn, and thereby enhancing skin and membrane cell proliferation and fortification, thus reducing scar tissue as well. Linoleic acid allows the formulation to maintain the epidermal barrier.

The formulations based on Emu oil accelerates wound closure, reduces wound debridement, reduces scar tissue and enhances the smoothness and appearance to the skin while maintaining and feeding skin cells with linoleic acid. The formulations can increases cell proliferation, therefore increasing the ability to heal.

Stearic acid (octadecanoic acid) is a common long chain fatty acids found in combined form in natural animal and vegetable fats. Commercial stearic acid is a mixture of approximately equal amounts of stearic and palmitic acids and small amounts of oleic acid. In nature, stearic acid occurs primarily as a mixed triglyceride, or fat, with other long-chain acids and as an ester of fatty alcohol. Stearic acid is much more abundant in animal fat than in vegetable fat; lard and tallow often contain up to 30 percent stearic acid. The embodied formulations can include stearic acid.

The composition and structure of the fatty acids of the naturally occurring lipids have an even number of carbon atoms because they are synthesized from acetyl groups, each of which contains two carbon atoms. Fatty acids with 16 (palmitic acid) and 18 (stearic acid) carbon atoms are most commonly found in nature, but the reasons for their abundance have not yet been established. Fatty acids constitute important components of lipids in plants, animals and microorganisms. In most cases, fatty acids are not found in free form, but instead are bound to other compounds to form fatty acid containing lipid (for example, neutral lipids (triglycerides) sterols, phosphoglycerides such as lecithin, and sphingolipids such as sphingomyelin).

Two typical fatty acids are oleic and palmitic. Although palmitic acid and stearic acid are the major saturated fatty acids found in animal and plant tissues, significant amounts of other saturated fatty acids such as myristic acid and lauric acid, occur in certain tissues, and lignoceric acid and behenic acid are found in high concentrations in brain sphingolipids. Small amounts of fatty acids with an odd number of carbon atoms are also known (for example, pentadecanoic acid and heptadeconoic acid).

Emu oil has been used in many preparations over the years for all types of skin complaints and maintenance. Emu oil has a positive effect on chronic cutaneous ulcers and burn wounds. Since a wound represents a breach in the body's natural barrier to microbial as well as fungal invasion, the final formulation of topical products used for the treatment of chronic cutaneous ulcers and burn wounds should be sterile to avoid introducing exogenous microorganisms. With this in mind, a product that could be sterilized for chronic cutaneous ulcers and burn wounds that could contain a high amount of Emu oil would be favorable for the industry. With respect to wounds and burns in general, a spray product would be favorable to avoid touching sensitive areas associated with various wounds, chronic cutaneous ulcers and burn wounds.

The embodied formulations can be used for chronic cutaneous ulcers, which also includes and addresses venous stasis ulcers, diabetic foot and leg ulcers, diabetic ulcers from neuropathy, pressure ulcers, graft sites, donor sites and all degrees of burn wounds. The embodied formulations are sterile formulations based upon the FDA's submission Documentation for Sterilization Process Validation for Human and Veterinary Drug Products (November 1994), which is hereby incorporated by reference.

The embodied formulations can be used to reduce debridement on tissue. Necrotic tissue inhibits wound healing by interfering with tissue repair and promoting microbial as well as fungal growth. Thorough debridement of wounds is therefore considered standard care essential to healing. The embodied formulations can be used in wound pain control.

The embodied formulations can be a spray on product (which is sterilized), a germicide, a bactericide, an antiseptic, an antifungal, and a bacteriastatic agent. If a spray on is used, additional environmentally friendly propellants can be added to the formulations. The embodied formulations can be modified as a transdermal formula, an enhanced oil, a spray, an elastomeric device, a wipe, a lotion, an ointment, a cream, a gel and the like.

The embodied formulations can inhibit the adverse effects and allergic reactions to benzoin derivatives as well as external analgesics.

The present formulation consists of Emu oil as a transdermal facilitator and other components that act to provide effective transport across the dermis or mucous membranes. The components can reduce necrotic tissue and can reduce and fight the infection that is in tissue, and keep tissue from growing fungus, or going into sepsis. The Emu oil and components also act as an anti-inflammatory agent.

The embodied formulations can include analgesic, anesthetic, and anti-pruritic ingredients. The embodied formulations can contain antimicrobial agents for wound infection control, a topical anti-infective, and elimination of microbial growth and necrotic tissue, which interferes with tissue repair. In addition, the formula can include a topical analgesic/anesthetic at active levels as set by FDA, and act as a topical pain control product.

Benzyl alcohol, a bezoin derivative, is listed in a summary of ingredient categories and testing as a category 1 analgesic, anesthetic, and anti-pruritic active ingredient. Other examples of bezoin derivatives are NF Benzenemethanol, phenyl carbinol CH2OH, and Benzyl C7H8, which are also known as benzyl alcohol. The benzyl alcohol, which can be used within the scope of the formulation, involves using esters of benzoic and cinnamic acids in storax, Peruvian balsam, and tolu balsam. A product currently on the market can be used which is made synthetically from benzyl chloride by distilling it from an aqueous solution of potassium carbonate with thorough agitation.

Benzyl Alcohol can be added in weight percents ranging from 0.10 to 33 percent. In one embodiment, the formulation can include 20.0 wt % benzyl alcohol for animals and 10.0% for humans. The formulation can further include an aromatic alcohol, in amounts from 0.5 to 1.2 wt %, which can be used in a concentration of 0.9% as a bacteriastatic preservative in multiple dose vials of solution or drugs for parenteral therapy. An aromatic alcohol such as Benzyl Alcohol can be used.

The embodied formulations can include using a local anesthetic by injection and by application to mucous membranes. Externally, the formula can be applied as an ointment or as a lotion in topical preparations and used as a bacteriastatic agent in various parenteral preparations. In addition to a spray formulation, externally the formula can also be applied to nasal passages and gum tissues.

Various antimicrobial drugs can be added to the Emu oil, including but not limited to: methylparaban or a benzoic acid, or an alkyl ester such as 4-hydroxy-, methyl ester; or possibly Solbrol made by Charkit Chemical Corporation, P.O. Box 1725, Darien, Conn. 07407; Methyl Parasept made by Charkit Chemical Corporation, P.O. Box 1725, Darien, Conn. 07407; Nipagin or even a Methyl p-hydroxybenzoate (99-76-3) C8 H8 O3 An antimicrobial additive can be formed by esterifying para-hydroxybenzoic acid with methanol using known techniques. The para-hydroxybenzioc acid is obtained by passing carbon dioxide under pressure into dry potassium phenolate heated to about 200 degrees. The resulting potassium salt is decomposed with HCl yielding the free parabic acid. These components can be added in amounts ranging from 0.25-1.25 wt %. Additional preservatives can be added to the formula such as Imidazolidinyl Urea in concentrations ranging from 0.05 to 1.0%.

Methylparabens and other related esters are para-hydroxybenzoic acids that are odorless and harmless to the skin can be employed in the formula. A combination of two or more esters of para-hydroxybenzoic acid has a "synergistic" antiseptic value, i.e. the antiseptic effect of the combination is greater than the total effect as calculated from the values of the individual components; thus a preparation containing 0.15% of the propyl ester also known as propylparaben and 0.05% of the benzoin derivative with a branched alkyl ester has a stronger antiseptic value than 0.2% of either ester alone. The benzoin ester has a high antiseptic value and is suitable for the preparation of antiseptic creams. As an example alkyl ester can be in the formulations in is between 1 wt % and 13 wt % (for, example 3.0 wt %).

Parahydroxybenzoic acid esters and mixtures of methylparaben and propylparaben can be used in the formulation with excellent and unexpected results. In the embodied compositions, the parahydroxybenzoic acid esters and mixtures of methylparaben and propylparaben can be used in a range of 0.025 wt % and 0.2 wt % of methylparaben (example range—0.1 wt % and 01.25 wt %); and propylparaben in the range of 0.01 wt % and 0.4 wt % (example range—between 0.3 wt % and 0.4 wt %).

Specific benzoic acids having between twelve and fifteen carbon atoms and alkyl esters can be added to an embodiment for the formula. For example, flowers of Benzoin; flowers of Benjamin; Phenylformic Acid, and Benzoic Acid, $C_7H_6O_2$, can be used. Benzoic Acid is the simplest acid of the aromatic series. Although the acid is of minor significance as a medicinal agent, the acid derivatives and salts constitute an important group of valuable medical agents. The addition of this component to the formula, enables the formulation to act as an antifungal agent chiefly in combination with benzyl alcohol as well as being an anesthetic. When the Emu oil contains enough benzyl alcohol and propylparaben it can then be used as an antifungal treatment for athletes' feet as well as several types of ringworm and other fungal skin irritations, which afflict humans and animals. Benzoin and its derivatives can be used in amounts between 0.10.0%-33.0 wt % (example amounts—10.0 wt % for human use and 20.0% for animals).

Allantoin can also be used (for example, Allantoin-5-Ureidohydantoin, $C_4H_6N_4O_3$). Allantoin is used topically as a vulnerary to stimulate tissue repair in suppurating wounds, resistant ulcers, acne seborrhea, and basic dermatological infections. Allantoin is included in some topical preparations for oral and dental use. Allantoin is frequently combined with antiseptics and antifungal drugs. The silver salt is used in the topical treatment of extensive burns. From about 0.2 wt % to about 2.0 wt % of Allantoin can be used, particularly when the formulation is used as creams, lotions or shampoo.

The formulation uniquely can be sterilized. Traditionally, sterilization has broken down the components of oils, which contain these types of fatty acids. The objective of a sterilization process is to remove or destroy all microorganisms in or on a preparation and to assure in this way the preparation is free of infectious hazards when used with a patient. Since the variety and amounts of the sterile materials required for health care have increased in significant proportions, sterilization technology has become increasingly important. Alternatively, if sterilization of the oil is not preferred, then a disinfectant can be added to the formula to render the skin noninfectious. A usable disinfectant can be an antiseptic or a germicide.

The embodied formulations can be a spray on transdermal formula having the additional transdermal effect of promoting the transdermal delivery of additional antiseptic, antifungal, and pain relieving medicine, thereby proliferating new skin cell growth and development.

Healing of a skin wound in mammals and animals is a mixture of regeneration, replacement, or substitution of a new cell type for an old one. Scarring is the result of replacement. If more cells are regenerated, less scarring will result after the wound is healed.

Wound healing typically follows a fairly typical time course in mammals. The presence of pathogens can lengthen the recovery time (Hackam and Ford, 2003). Generally, within a few minutes of the initial damage to the tissue a plug of platelets and other blood products, also known as blood clots, form at the site of tissue damage and stops further loss of blood.

Within hours of receiving the wound, debris-eating white blood cells called neutrophils invade the area of damage, signaling the start of the inflammation response. Inflammation is a series of events that includes increased blood flow, increased blood vessel permeability, activation of pain receptors, and intense consumption of cell debris and bacteria by neutrophils and other white blood cells. Neutrophils ingest introduced bacteria and dead and dying cells in the wound. Neutrophils are themselves killed in the process. The accumulating mixture of dead neutrophils and fluid forms pus. Within a few days, the surface of the clot has dried to form a scab. Now macrophages, which are another type of specialized white blood cell, infiltrate the wound and ingest dead neutrophils and other cellular debris.

Within a week after the wound occurred, tough, fibrous cells called fibroblasts move in from surrounding connective tissue and start to multiply at the wound site. The fibroblasts begin to secrete collagen fibers. At the same time, new epidermis begins to regenerate. New endothelial cells from neighboring undamaged tissue begin to form new capillaries that grow into the repairing wound site to supply blood to the newly forming epidermis.

Within a few weeks, the rapidly dividing epidermis completely lines the original wound site. The fibroblasts generate new connective tissue or scar tissues, which replaces the epidermis destroyed by the wound. Scar tissue persists after the healing of particularly severe wounds.

The speed and effectiveness of skin wound repair depends on several factors (Burns et al., 2003). Proper nutrition is essential (Russell 2001). Vitamins C, D, E, and K all play important roles at some stage in the tissue repair process (Casey, 2003). Agents that increase cell division, such as the Emu oil found in the present formulation, also hasten wound healing (Snowden et al., 1997; Politis and Dmytrowich, 1998; Lopez et al., 1999).

The oleic-rich Emu oil within the present formulation enables epidermal tissue to regenerate, restore, and rebuild in the wound itself and in underlying dermal and subcutaneous tissue. The effect of the oleic-rich Emu oil fortifies the non-necrotic epidermal and dermal cells and revitalizes potential necrotic cells. (Snowden et al., 1997; Politis and Dmytrowich, 1998; Lopez et al., 1999). A major clinical benefit of the present formulation is the reduction of the wound sepsis rates due to the formulations clinically proven antibacterial and antifungal properties.

The embodied formulations can provides improved rates of wound closure, including surgical incisions and reduced healing times. The formulations can reduce wound debridement and increase epidermal cell proliferation, while maintaining and feeding skin cells with linoleic acid. The development of proud flesh, a common ailment in wound treatment in horses, is retarded or even prevented using the embodied formulations. Reduced scarring is evident, leading to improved function such as range of motion, contour and profile of healed skin, normalization of skin pigmentation, markings as well as hair regrowth.

The applicants recently sponsored an investigation at a microbiology laboratory at the University of North Texas located in Denton, Tex. The investigation has conclusively proven that the present formulation has statistically significant, and potent, anti-bacterial properties. The composition is especially effective against *Staphylococcus aureus, Enterococcus faecalis*, and *Pseudomonas aeruginosa*, which are three common pathogens in animal and mammal wounds.

A variety of *Escherichia coli* bacteria are present in nature. They are usually found in the intestines of healthy humans and healthy animals. Even though these bacteria offer beneficial properties, there are those variations, or strains, that are pathogenic or have the ability to cause disease. *Escherichia coli* 0157:H7 is one particular strain that is also an emerging cause of foodborne illness. Symptoms such as bloody diarrhea and abdominal cramps can be observed or no such symptoms can appear. The elderly and children under five years old are highly susceptible to Hemolytic Uremic Syndrome, a disease in which red blood cells are destroyed and kidneys fail (Kendrick & Wrobel-Woerner, 1997).

The *Salmonella* germ is actually a group of bacteria that can cause diarrhea illness in humans. They are microscopic living creatures that pass from the feces of people or animals, to other people or other animals. There are many different kinds of *Salmonella* bacteria. *Salmonella* serotype *Typhimurium* and *Salmonella* serotype *Enteritidis* are the most common in the United States. *Salmonella* has been known to cause illness for over 100 years. Many different kinds of illnesses can cause diarrhea, fever, or abdominal cramps. Determining that *Salmonella* is the cause of the illness depends on laboratory tests that identify *Salmonella* in the stools of an infected person. These tests are sometimes not performed unless the laboratory is instructed specifically to look for the organism. Once *Salmonella* has been identified, further testing can determine the specific type of *Salmonella*, and which antibiotics could be used to treat the specific type.

*Pseudomonas aeruginosa*, a versatile Gram-negative bacterium, grows in soil, marshes, and coastal marine habitats, as well as on plant and animal tissues. The bacterium *Pseudomonas aeruginosa* causes significant infections in humans. People with cystic fibrosis, burn victims, individuals with cancer, and patients requiring extensive stays in intensive care units are particularly at risk.

*Staphylococcus aureus* is the most common cause of food borne illness. Commonly called staph, this bacterium produces a poisonous toxin that causes the illness. Symptoms of staphylococcal food poisoning are usually rapid and in many cases serious, depending on individual response to the toxin, the amount of contaminated food eaten, the amount of toxin in the food ingested, and the general health of the victim. The most common symptoms are nausea, vomiting, abdominal cramping, and prostration. Some individuals do always demonstrate all the symptoms associated with the illness. In more severe cases, headache, muscle cramping, and changes in blood pressure and pulse rate can occur. Recovery generally takes two days. Complete recovery can take three days and sometimes longer.

The *enterococcus* previously *Streptococcus faecalis*, causes many of the same problems as other members of the intestinal flora. These include opportunistic urinary tract infections and wound infections. In contrast to the Enterobacteriaceae, enterococcal infection is often associated with bacteria, which can lead to endocarditis or colonization of previously damaged heart valves. Little is known about its pathogenesis. The D in an older name, group D strep, refers to the Lancefield classification which is based on the antigenicity of a carbohydrate which is soluble in dilute acid and called the C carbohydrate. Lancefield identified 13 types of C carbohydrate, designated A through 0, which could be serologically differentiated. The organisms that most commonly infect humans are found in groups A, B, D, and G. Streptococci that do not contain the C carbohydrate substance are called viridans streptococci or non-typable streptococci.

*Bacillus cereus* has been recognized as an agent of food poisoning since 1955. Between 1972 and 1986, 52 outbreaks of food-borne disease associated with *B. cereus* were reported to the CDC, but this is thought to represent only 2% of the total cases, which have occurred in that time. *Bacillus cereus* causes two types of food-borne intoxications as opposed to infections. One type is characterized by nausea and vomiting and abdominal cramps and has an incubation period of 1 to 6 hours. *Bacillus cereus* resembles *Staphylococcus aureus* food poisoning in its symptoms and incubation period (the short-incubation or emetic form of the disease). Nonanthrax *Bacillus* species, especially *Bacillus cereus*, are occasionally implicated in local infections especially involving the eye. Nonanthrax *Bacillus* species can cause conjunctivitis, keratitis, iridocyclitis, dacryocystitis, orbital abscess, and panophthalmitis. The usual setting is that of previous occurrence of penetrating nonsurgical trauma. An intra-ocular foreign body such as a metal projectile is often present, or the injury occurs in a rural or farm location where there is a greater risk of eye contamination with dust or soil. *Bacillus cereus* is one of the most destructive organisms to infect the eye.

*Candida albicans* is one of the most commonly encountered human pathogens, causing a wide variety of infections ranging from mucosal infections in generally healthy persons to life-threatening systemic infections in individuals with impaired immunity. Oral and esophogeal *Candida* infections are frequently seen in AIDS patients. Few classes of drugs are effective against these fungal infections, and all of them have limitations with regard to efficacy and side effects. *Candida albicans* is also the major fungal pathogen of humans. Infections can be localized, such as vaginal infections and oral infections, which cause a considerable degree of discomfort. In some patient groups, whose defense system is severely compromised, as in prematurely born infants, leukemics and burn patients, the yeast can turn into a deadly pathogen causing systemic infections, up to 50% of the patients infected die as a result.

The incidence of such infections is increasing rapidly, especially in hospitalized patients. In New Zealand, such infections are now eight times more frequent than they were 9 years ago. The current reservoir of anti-Candida drugs is very limited, and these agents can have severe side effects. Development of new strategies for the prevention and treatment of candidiasis is therefore probably the most important challenge to be faced by medical mycology today. One of the prerequisites to developing such strategies is the knowledge of how *Candida albicans* causes disease. Until recently the prevailing assumption was that *Candida* infections are simply caused by strains already present on the patient as commensals.

Using computer-assisted DNA fingerprinting with the probe Ca3, the most accurate *Candida albicans* typing method currently available, a vast amount of evidence is present to challenge this view. It seems that commensal strains are frequently replaced by other, more aggressive strains, derived from a single group of ubiquitous strains, regardless of geographic region or patient type prevalence. These strains seem responsible for approximately one third to half of all *Candida* infections worldwide. Our evidence suggests that these strains can not only be more virulent but also more resistant to antifungal drugs than other strains.

*Streptococcus agalactiae* is a gram-positive obligate pathogen that affects pre-milking heifers, as well as older cows in dairy herds. *Streptococcus agalactiae* is a major cause of economic losses to dairy producers without a control program. Although *Streptococcus agalactiae* can live outside the udder for short periods of time in the right conditions, *Streptococcus agalactiae* is considered to be an obligate pathogen of the udder. A high percentage of cows can be affected in herds where control procedures are not implemented. Fomites such as strip cups, towels, milkers hands, cross suckling calves, milking machines and other milking equipment and unsanitary conditions are all potential sources of infection in cows. Even mastitis preparations can be a potential source of infection for the udder.

*Streptococcus agalactiae* can be transmitted from udder to udder in many ways. *Streptococcus agalactiae* breaks the natural barriers of the udder, enters the teat canal, and ascends in the milk through the quarter. The bacterium penetrates the acinar epithelium, causing edema and extravasation of neutrophils into the lumen, resulting in subclinical or clinical mastitis as well as possible systemic infection. In later stages, the acini become filled with scar tissue, which plugs the glandular-ductal system resulting in a chronic, smoldering infection, which decreases milk production and increases the somatic cell count of the quarter. Poor udder health due to *Streptococcus agalactiae* is slowly progressive over time, causing fibrosis and atrophy of the affected quarter. An individual cow with a high somatic cell count typically has lower production that correlates with increased somatic cell count of the herd.

The following test results were conducted on the embodied formulations. The project that produced the results was performed D. A. Kunz, Ph.D., Department of Biological Sciences at the University of North Texas, Denton. The organisms tested included *Escherichia coli*, *Salmonella typhimurium*, *Pseudomonas aeruginosa*, *Staphylococcus aureus*, *Enterococcus faecalis*, *Bacillus cereus*, *Candida albicans*, and *Streptococcus agalactiae*.

The test involved growing test cultures of inocula. All bacteria were grown as shelf cultures at 37° C. with the exception of *Candida albicans* that was grown at 30° C. The medium was Mueller-Hinton (M-H), which is the standard used for antimicrobial susceptibility testing.

The test samples were added to sterile diluted liquid culture medium such that after addition the total volume was 5 ml (see below). All tubes were then inoculated with 0.1 ml of an overnight broth culture (~1–2×10$^6$ cells [CFU]) and growth determined after 24 h by reading the culture turbidity with a spectrophotometer. The MIC is defined as the lowest concentration of the Emu oil composition inhibiting growth as evidenced by a lack of detectable turbidity.

Table 2 is the standard dilution scheme used in the test:

TABLE 2

Standard Dilution Scheme

|  | 10X M-H | Water | Sample |
|---|---|---|---|
| 0% Concentration | 0.5 | 4.50 | 0 |
| 5% Concentration | 0.5 | 4.25 | 0.25 |
| 2% Concentration | 0.5 | 4.40 | 0.10 |
| 1% Concentration | 0.5 | 4.45 | 0.05 |
| 0.5% Concentration | 0.5 | 2 | 2.5 of 100 |
| 0.2% Concentration | 0.5 | 3.5 | 1.0 of 100 |
| 0.1% Concentration | 0.5 | 4.0 | 0.5 of 100 |

Table depicts the results of the liquid culture test.

TABLE 3

Liquid Culture Test Results

| | | Turbidity (Growth) at a Concentration (MIC†) | | | | |
|---|---|---|---|---|---|---|
| | | 0 | 0.5% | 1% | 5% | |
| *Escherichia coli* JM101 A | 1 day | 1.351 | 1.024 | 0.516 | 0.045 | 2% |
| *Escherichia coli* JM101 B | 1 day | ND | 1.002 | 0.408 | 0.058 | 2% |
| *Enterococcus faecalis* A | 1 day | 0.961 | 0.473 | 0.209 | 0.020 | 2% |
| *Enterococcus faecalis* B | 1 day | ND | 0.478 | 0.229 | 0.046 | 2% |
| *Pseudomonas aeruginosa* A | 1 day | 0.607 | 0.648 | 0.368 | 0.024 | 2% |
| *Pseudomonas aeruginosa* B | 1 day | ND | 0.886 | 0.560 | 0.021 | 2% |
| *Salmonella typhimurium* A | 1 day | 1.199 | 0.838 | 0.453 | 0.030 | 2% |
| *Salmonella typhimurium* B | 1 day | ND | 0.749 | 0.270 | 0.016 | 2% |
| *Staphylococcus aureus* A | 1 day | 0.760 | 0.547 | 0.518 | 0.009 | 5% |
| *Staphylococcus aureus* B | 1 day | 0 | 0.582 | 0.475 | 0.004 | 5% |
| *Bacillus cereus* A | 1 day | 0.500 | 0.768 | 0.673 | 0.034 | 5% |
| *Bacillus. cereus* B | 1 day | ND | 0.900 | 0.661 | 0.048 | 5% |
| *Candida albicans* A 30° C. | 1 day | 0.411 | 0.506 | 0.100 | 0.11 | 5% |
| *Candida albicans* B 30° C. | 1 day | ND | 0.624 | 0.182 | 0.06 | 5% |
| *Streptococcus agalactiae* A | 1 day | 0.467 | 0.394 | 0.316 | 0.064 | 5% |
| *Streptococcus agalactiae* B | 1 day | ND | 0.387 | 0.340 | 0.074 | 5% |

In Table 3e, the values represent turbidity (growth) measurements at 540 nm. The reference blanks contained sterile medium with the Emu oil composition at the concentrations shown less cells. The identification ND stands for "not determined" and the identification MIC stands for "Minimal Inhibitory Concentration".

Other tests completed comprised a solid plate or spray test. Sprayed plates with the Emu oil composition were tried and compared the number of survivors in the presence and absence of agent with Staph, Pseud and Entero but no significant differences in viability were experienced.

The conclusion from the tests is that the Emu oil composition showed high antimicrobial activity at relatively low concentrations of the Emu oil composition.

The embodied formulations have shown to be effective against the treatment of suspected chronic fungal infections in addition to acute wounds.

The applicants recently conducted an additional study of antifungal tests of the formulation, which were carried out in the laboratories of the Center for Medical Mycology, Case Western Reserve University, Cleveland, Ohio, USA, to assess the specific antifungal properties of the formulation in a controlled laboratory setting. Fungal dermatophytes infect horses, dogs and cats and can readily cross over to humans (Kerl, 2003). The investigation has conclusively proven that the present formulation has statistically significant, and potent, antifungal properties. The formulation is especially effective against *Trichophyton rubrum*, *Microsporum equinum*, *Trichophyton equinum*, *Microsporum gypseum*, *Microsporum canis*, *Epidermophyton floccosum*, *Trichophyton mentagrophytes* in animal and mammal wounds.

The following common, pathogenic fungi were used and acquired from the culture collection at the Case Western Reserve University or purchased from the American Type Culture Collection (ATCC) and tested in this study as follows: *Trichophyton* rubrum ATCC 28188, *Microsporum equinum* ATCC 42906, *Trichophyton* equinum ATCC 22443, *Microsporum gypseum* ATCC 102588, *Microsporum canis* CAP F04-03, *Epidermophyton floccosum* ATCC 52066, *Trichophyton mentagrophytes* ATCC 24953. These fungi are very common pathogens in domesticated animals and humans, responsible for many of the most common forms of dermatophytosis (Hainer, 2003). *Trichophyton*, for example, is one of the leading causes of hair, skin, and nail infections in humans, including scalp ringworm also known as tinea capitis. *Microsporum canis* is the most common cause of ringworm in dogs and cats, and is commonly transmitted to humans by an infected animal or mammal.

The minimum inhibitory concentration (MIC) of the present formulation against each fungal isolate was determined according to the modification of NCCLS method for susceptibility testing of dermatophytes developed at the Center for Medical Mycology (Jessup et al., 2000).

A 1:1 dilution was first prepared in DMSO in order to dissolve the formulation spray. Serial dilution sprays were then made in the cell culture medium RPMI 1640 (BioWhittaker Inc.) in a range of 25-0.1%. Cultures were incubated for 4 days at 35° C. Inoculum size was 1–3×103 conidia/ml.

Data were expressed as the minimal inhibitory concentration (MIC), which is defined as the lowest concentration of the present formulation inhibiting all fungal growth. Inhibition of fungal growth was also determined as the amount of inhibition compared to growth of the control cultures (no exposure to the present formulation).

The embodied formulations showed highly potent antifungal properties against all seven species tested. Almost total fungal suppression occurred at the present formulation concentrations as low as 0.4% in most fungi tested. *Trichophyton rubrum* and *Microsporum equinum* were even more susceptible, showing MICs at concentrations as low as 0.2% of the embodied formulations. Table 4 is the minimal inhibitory concentrations of the embodied formulations in eight microorganisms.

TABLE 4

Minimal Inhibitory Concentrations of the Embodied Formulations

| Fungus | MIC (%) |
|---|---|
| *Trichophyton rubrum* | 0.2 |
| *Microsporum equinum* | 0.2 |
| *Trichophyton equinum* | 0.4 |
| *Microsporum gypseum* | 0.4 |
| *Microsporum canis* | 0.4 |
| *Epidermophyton floccosum* | 0.4 |
| *Trichophyton mentagrophytes* | 0.4 |

Growth inhibition can be expressed as the amount of inhibition compared to growth control, as shown in Table 5. Again, even in concentrations as little as 0.4% the present formulation caused nearly complete inhibition of growth of these common dermatophytes. Table 5 is the comparative inhibitory growth of fungal cultures following exposure to the embodied formulations.

TABLE 5

Comparative Inhibitory Growth of Fungal Cultures Following Exposure to the Embodied Formulations

| Fungus | Comp. Inhibition (%) |
|---|---|
| *Trichophyton rubrum* | 100% |
| *Microsporum equinum* | 100% |
| *Trichophyton equinum* | 100% |
| *Microsporum gypseum* | 80% |
| *Microsporum canis* | 100% |
| *Epidermophyton floccosum* | 100% |
| *Trichophyton mentagrophytes* | 80% |

In vitro, the embodied formulations show highly effective suppression of the growth of common dermatophytic fungus. Minimal inhibitory concentrations (MIC) varied slightly, but all MICs were 0.4% or less for the seven fungal species tested.

In vitro testing in this study involved high dilutions of the present formulation in the test medium, which is a typical laboratory procedure for in vitro testing of antifungal properties. How these in vitro data relate to the actual concentration of the present formulation occurring when the formulation is topically applied in full strength to a wound as directed has not been determined. However, since the present formulation is applied at full strength, or 100% concentration in human and veterinary applications, the concentration of the present formulation experienced by pathogens on the surface tissues of wounds or infections is likely to be very high, and certainly much higher than the effective MICs reported in this study.

In conclusion, the embodied formulations have significant antifungal properties in vitro in a wide range of fungal dermatophytes common in both veterinary and human infections.

References—Hainer, B. L. 2003. Dermatophyte infections. Am. Fam. Physician. 67(1):101-8; Jessup, C. J., Warner, J., Isham, N., Hasan, I., and Ghannoum, M. A. 2000; Antifungal susceptibility testing of dermatophytes: establishing a medium for inducing conidial growth and evaluation of susceptibility of clinical isolates; J. Clin. Microbiol. 38:341-344; Kerl, M. E. 2003; Update on canine and feline fungal diseases; Vet. Clin. North Am. Small Anim. Pract. 33:721-47; Pomeranz A. J. and Sabnis, S. S. 2002; Tinea capitis: epidemiology, diagnosis and management strategies; Paediatr Drugs. 4:779-83.

Dermatophytes are fungi that can cause infections of the skin, hair, and nails due to their ability to utilize keratin. The organisms colonize the keratin tissues and inflammation is caused by host response to metabolic by-products. These infections are known as ringworm or tinea, in association with the infected body part. Occasionally the organisms do invade the subcutaneous tissues, resulting in kerion development. The organisms are transmitted by either direct contact with infected host, human or animal or by direct or indirect contact with infected exfoliated skin or hair in combs, hair brushes, clothing, furniture, head coverings, bed linens, towels, rugs, and locker room floors. Depending on the species the organism can be viable in the environment for up to 15 months. There is an increased susceptibility to infection when there is a preexisting injury to the skin such as scars, burns, as well as excessive temperature and humidity. Dermatophytes are classified as anthropophilic, zoophilic or geophilic according to their normal habitat.

Anthropophilic dermatophytes are restricted to human hosts and produce a mild, chronic inflammation. Zoophilic organisms are found primarily in animals and cause marked inflammatory reactions in humans who have contact with infected cats, dogs, cattle, horses, birds, or other animals. Geophilic species are usually recovered from the soil but occasionally infect humans and animals. They cause a marked inflammatory reaction, which limits the spread of the infection but can leave scars.

The dermatophytes consist of three genera: *Epidermophyton* produces only macroconidia and consists of two species, one of which is a pathogen. *Microsporum*; both microconidia and rough-walled macroconidia characterize *Microsporum* species. There are nineteen described species but only nine are involved in human or animal infections. *Trichophyton*, when produced the macroconidia of *Trichophyton* species are smooth-walled. There are twenty-two species, most causing infections in mammals or animals.

At the National Centre for Mycology about 58.0% of the dermatophyte species isolated are *Trichophyton Rubrum*, 27.0% are *T. Mentagrophytes*, 7.0% are *T. Verrucosum*, 3.0% are *T. Tonsurans*. Infrequently isolated at less than 1.0%, are *Epidermophyton foccosum, Microsporum audouinii, M. Canis, M. equinum, M. nanum, M. persicolor, Trichophyton equinum, T. kanei, T. raubitschekii*, and *T. violaceum*.

*Trichophyton rubrum* ATCC 28188. The genus *Trichophyton* is a dermatophyte, which inhabits the soil, humans or animals. Related to its natural habitats, the genus includes anthropophilic, zoophilic, and geophilic species. *Trichophyton* is one of the leading causes of hair, feather, skin, and nail infections in humans and animals, such as dogs, cats and horses and birds. The taxonomic classification is as follows; Kingdom: Fungi; Phylum: Ascomycota; Class: Euascomycetes; Order: Onygenales; Family: Arthrodermatacea; Genus: *Trichophyton; Teleomorph: Arthroderma*.

Pathogenicity and Clinical Significance of *Trichophyton, Microsporum*, and *Epidermophyton* are the causative agents of dermatophytosis and infect the hair, skin, and nails. Similar to the other two genera, *Trichophyton* is a keratinophilic filamentous fungus. Ability to invade keratinized tissues and the possession of several enzymes, such as acid proteinases, elastase, keratinases, and other proteinases and are the major virulence factors of these fungi. *Trichophyton rubrum* is the commonmost causative agent of dermatophytoses worldwide. *Trichophyton* species can cause invasive infections in the immunocompromised.

Many medications such as ketoconazole, clotrimazole, itraconazole, terbinafine, naftifine, and amorolfine are in general active in vitro against *Trichophyton*.

Griseofulvin, once the drug of choice for treatment of dermatophytosis, is now less commonly used due to the availability of more effective and less toxic drugs. Terbinafine and itraconazole are now commonly used in treatment of infections due to *Trichophyton* and other dermatophytes. For treatment of tinea capitis and onychomycosis, oral therapy is usually preferred.

The embodied formulations provide a product that can easily be administered externally without prescription and harmful side effects such as toxicity would be preferable for the consumer and the environment.

*Microsporum equinum* ATCC 42906 is a rare cause of ringworm of horses and can infect man or other animal species. *Microsporum equinum* ATCC 42906 is one of the most important skin diseases of horses found throughout the world. Several species of fungus can cause the condition, but *Trichophyton equinum, Trichophyton mentagrophytes* and *Microsporum equinum* are most common.

The disease is spread by direct horse contact or indirectly via communal grooming equipment and tack. Young horses are more susceptible due to lack of previous exposure or immunity. After exposure resistance does occur, however in regards to the fact there are several fungal species that could be responsible and since immunity is not life long, re-infection can occur. Ringworm is highly transmissible to humans since ringworm is a zoonotic disease. Lesions are localized, often circular and consist of areas of hair loss with reddening of the skin, itching, flaking and scab formation. The infection is best treated due to its contagious nature. Topical antifungal creams are available as well as systemic antifungals that are ingested orally.

The embodied formulations provide a product that can quickly and topically relieve the contagious infection would be preferable to prescription topical creams and costly oral systemic antibiotics.

*Trichophyton equinum* ATCC 22443 is a zoophilic fungus causing ringworm in horses and infections in humans. Human *Trichophyton equinum* infection is typically treated with terbinafine for a usual six-week course of treatment with the allyl amine antifungal agent, terbinafine.

*Microsporum gypseum* ATCC 102588 is a geophilic fungus with worldwide distribution causes infection in animals and humans, particularly children and rural workers during warm humid weather. A single inflammatory skin or scalp lesion is usually produced. Clinical group: Cutaneous mycoses; Mycosis: Dermatophytosis

*Microsporum* is one of the three genera that cause dermatophytosis. *Microsporum*, similar to other dermatophytes, has the ability to degrade keratin and thus can reside on skin and its appendages. The keratinase enzyme, proteinases and elastases of the fungus can act as virulence factors. *Microsporum* mostly infects the hair and skin, nail infections can occur.

Terbinafine and itraconazole appear active in vitro against *Microsporum*. However, this fungus was found to be the least terbinafine-susceptible dermatophyte in vitro, even so, oral therapy with terbinafine and itraconazole are very widely used for treatment of *Microsporum* infections. Griseofulvin was once the drug of choice for treatment of infections due to *Microsporum* as well as other dermatophytes, however, safer and more efficacious alternatives would be preferred.

The embodied formulations provide a product that can be effectively and safely used against *Microsporum* and can be used topically as opposed to an orally ingested medication would be preferable.

*Microsporum canis* CAP F04-03. *Microsporum canis* is a zoophilic dematophyte of world-wide distribution which is a frequent cause of ringworm in humans, especially children and infests hair, skin and nails.

The natural reservoir of *Microsporum canis* is cats and dogs. *Microsporum canis* causes tinea capitis and tinea corporis in humans and other affected animals are horses, cows, and other animals. Ringworm can be transmitted between humans and animals.

The fungal skin disease dermatophytosis is called ringworm because of the appearance of the skin lesion that characteristically occurs with a circular area of hair loss with a red, raised outer rim. Resulting from inflammatory reaction to the fungus, these lesions occur. Most often, dogs and cats are infected by the *Microsporum canis* fungus, but humans and other animals and mammals can be effected by ringworm infections as well.

Cats, especially longhaired breeds, have a more generalized form of infection than dogs. These animals can be chronic carriers of a fungus even though they can not show any signs of infection themselves. These ringworm fungi can be transmitted to humans as well. Precautions should be taken while treating animals to prevent human infection and environmental contamination.

Treatment of affected animals or mammals for ringworm is by administration of tablets or systemic therapy and topical therapy treatment applied directly to the affected area. For systemic therapy, Griseofulvin is the drug most commonly used for the treatment of dermatophytosis and is the only antifungal medicine that is licensed for use in the cat. Griseofulvin should not be used in pregnant animals because it can cause fetal abnormalities. Pregnant women should avoid handling Griseofulvin. Griseofulvin can cause other unwanted side effects, if a cat receiving treatment with Griseofulvin becomes ill, its medicine should be stopped and veterinary advice sought. Cats with feline immunodeficiency virus infection (FIV) are much more susceptible to dangerous side effects and a screening test for FIV can be necessary before starting therapy. Alternative drugs are now available and can be used in cats that will not tolerate or are unresponsive to Griseofulvin. These are all human medicines, which are expensive.

Topical therapy can play a very important role in reducing environmental contamination. Spot therapy with one of the human antifungal creams is not recommended because the area of infected skin is often considerably wider than the skin lesions might suggest. Topical therapy is best applied to the whole body by either shampooing or dipping. Clipping of cats will make this much easier, particularly for longhaired cats, and also reduce environmental contamination. Clipping should be done carefully in order to avoid damaging the skin, as this can spread infection and make the skin lesions look worse for a short time. Normally the cats have to be sedated cats to clip them safely. Infected hair should be disposed of by burning and clippers should be decontaminated properly.

The embodied formulations provide a product that is safe for the environment and can be easily applied as effective protection against infection in cats. In a spray form, the embodied formulations can be easily used on longhaired species of felines without shampooing or the danger of clipping as well as the unwanted side effects of sedation or systemic therapy.

*Epidermophyton floccosum* ATCC 52066 is one of the three fungal genera classified as dermatophytes and is a filamentous fungus, which is distributed worldwide. The only species which is pathogenic, and known to cause infections in humans, man is the primary host of *Epidermophyton floccosum*, is one of the common causes of dermatophytosis in otherwise healthy individuals, infecting with skin with fungus such as tinea corporis, tinea cruris, tinea pedis and nail fungus such as onychomycosis. Epidermoph *floccosum* infections are able to be passed from one person, animal, or organism to another and transmitted by contact, especially in gym facilities and common showers.

*Trichophyton mentagrophytes* ATCC 24953 are anthrophilic and zoophilic, infecting rodents, small and large mammals, humans, large and small animals worldwide, are found in soil, feet, body, nails, beard, scalp, hand, and groin areas. *Trichophyton mentagrophytes* are zoophilic which are ectothrix and anthrophilic and do not infect hair. Fungal infections of foot are called athlete's foot. Athlete's foot is a chronic and recurrent dermatomycosis occurring at the toenails, and also the top and bottom of the foot. The fungus causing athlete's foot is *Trichophyton mentagrophytes*.

The embodied formulations can be used to treat athlete's foot. Currently, systemic oral dosage drugs are available and work while taking the systemic drug, but are very costly with recurring side effects and results are not typically seen in the short term. The embodied formulations, as a spray, can work effectively to treat athlete's foot and, since is not used orally like current methods, can beneficial to humans and animals.

The embodied formulations can be embodied in many forms without departing from the spirit or essential characteristics of the formulation. The embodiments are therefore to be considered in all respects as illustrative and not restrictive, the scope of the formulation being indicated by the appended claims rather than by the foregoing description. All changes, which come within the meaning and range of equivalency of the claims, are therefore intended to be embraced therein.

While only a few embodiments of the formulation have been disclosed in the above detailed description, the formulation is not limited thereto but is susceptible to various changes without departing from the scope of the formulation.

What is claimed is:

1. A formula for use in treating skin comprising:
   a. from about 20 to about 75 wt % emu oil;
   b. from about 0.01 to about 20.0 wt % caine anesthetics;
   c. from about 0.10 to about 33 wt % benzoin derivative;
   d. from about 0.2 to about 2 wt % allantoin;
   e. from about 0.25 to about 1.25 wt % methylparaben;
   f. from about 1.0 to about 13 wt % alkyl esters; and
   g. from about 0.01 to about 0.30 wt % propylparaben.

2. The formula of claim 1, wherein the formula is applied to the skin through an enhanced oil, a spray, an elastomeric device, a wipe, a lotion, an ointment, a cream, a gel or combinations thereof.

3. The formula of claim 1, wherein the formula is a topical anti-microbial formula.

4. The formula of claim 1, wherein the formula is a topical anti-fungal formula.

* * * * *